US011455721B2

(12) United States Patent
Jang et al.

(10) Patent No.: US 11,455,721 B2
(45) Date of Patent: Sep. 27, 2022

(54) MULTIWAVE DENTAL IMAGING SYSTEM

(71) Applicants: Andrew Timothy Jang, San Mateo, CA (US); Nai-Yuan Nicholas Chang, San Francisco, CA (US)

(72) Inventors: Andrew Timothy Jang, San Mateo, CA (US); Nai-Yuan Nicholas Chang, San Francisco, CA (US)

(*) Notice: Subject to any disclaimer, the term of this patent is extended or adjusted under 35 U.S.C. 154(b) by 187 days.

(21) Appl. No.: 16/779,021

(22) Filed: Jan. 31, 2020

(65) Prior Publication Data
US 2020/0250819 A1 Aug. 6, 2020

Related U.S. Application Data

(60) Provisional application No. 62/799,920, filed on Feb. 1, 2019.

(51) Int. Cl.
*G06T 7/00* (2017.01)
*A61B 5/00* (2006.01)
*A61C 9/00* (2006.01)

(52) U.S. Cl.
CPC .......... *G06T 7/0012* (2013.01); *A61B 5/0035* (2013.01); *A61B 5/0073* (2013.01);
(Continued)

(58) Field of Classification Search
CPC ................ G06T 7/0012; G06T 5/50; G06T 2207/10024; G06T 2207/10048; G06T 2207/10152; G06T 2207/20221; G06T 2207/30036; A61B 5/0035; A61B 5/0062; A61B 5/0073; A61B 5/0075; A61B 5/117; A61B 5/4547; A61B 5/742; A61B 5/7425;
(Continued)

(56) References Cited

U.S. PATENT DOCUMENTS 7,929,151 B2 * 4/2011 Liang ................. A61B 1/00186
356/601
9,494,418 B2 * 11/2016 Schmidt ................. G01B 11/25
(Continued)

OTHER PUBLICATIONS

Buhler et al., "Imaging of occlusal dental caries (decay) with near-IR light at 1310-nm", Optics Express, Jan. 24, 2005, vol. 13, No. 2, pp. 573-582 (Year: 2005).*
(Continued)

*Primary Examiner* — Nay A Maung
*Assistant Examiner* — Jose M Torres
(74) *Attorney, Agent, or Firm* — Schwegman Lundberg & Woessner, P.A.

(57) ABSTRACT

An imaging system comprises multiple light sources, a beam combiner, an optical array sensor, and a computing device. A first light source forms a first beam of light at a first wavelength. A second light source forms a second beam of light at a second wavelength. The beam combiner combines the first beam of light and the second beam of light into a single beam of light and illuminates a specimen with the single beam of light. The optical array sensor detects reflected light that is reflected from the specimen. The computing device accesses sensor data from the optical array sensor, forms a first image based on the first wavelength and a second image based on the second wavelength, and forms a composite image from the first image and the second image.

12 Claims, 13 Drawing Sheets

(52) U.S. Cl.
CPC .......... *A61B 5/0088* (2013.01); *A61B 5/4547* (2013.01); *A61B 5/7425* (2013.01); *A61C 9/0053* (2013.01); *A61B 2562/0238* (2013.01); *G06T 2207/30036* (2013.01)

(58) Field of Classification Search
CPC .......... A61B 2562/0238; A61B 5/0088; A61C 9/0053
See application file for complete search history.

(56) References Cited

U.S. PATENT DOCUMENTS

| | | | | |
|---|---|---|---|---|
| 10,123,706 B2* | 11/2018 | Elbaz | ................... | H04N 13/246 |
| 10,327,872 B2* | 6/2019 | Verker | ............... | G02B 23/2461 |
| 11,096,586 B1* | 8/2021 | Belthangady | ........ | A61B 5/0088 |
| 2005/0283065 A1* | 12/2005 | Babayoff | .............. | G01J 3/0218 |
| | | | | 600/407 |
| 2007/0134615 A1* | 6/2007 | Lovely | .................. | A61B 1/063 |
| | | | | 433/29 |
| 2010/0068673 A1* | 3/2010 | Yamada | ............... | G01N 21/474 |
| | | | | 433/29 |
| 2010/0311005 A1* | 12/2010 | Liang | ................... | A61B 5/1079 |
| | | | | 433/29 |
| 2011/0102566 A1* | 5/2011 | Zakian | ................ | A61B 5/0086 |
| | | | | 348/66 |
| 2011/0221880 A1* | 9/2011 | Liang | ................... | A61B 1/0607 |
| | | | | 348/E7.085 |
| 2014/0272767 A1* | 9/2014 | Monty | ................ | A61C 1/0046 |
| | | | | 433/29 |
| 2015/0164335 A1* | 6/2015 | Van Der Poel | ........ | A61B 5/742 |
| | | | | 433/29 |
| 2018/0249913 A1* | 9/2018 | Seibel | ....................... | G01J 3/10 |

OTHER PUBLICATIONS

Angelino et al., "Digital reconstruction of teeth using near-infrared light", 2019 41st Annual International Conference of the IEEE Engineering in Medicine and Biology Society (EMBC), pp. 4414-4418 (Year: 2019).*

Angelino et al., "Near-Infrared Imaging for Detecting Caries and Structural Deformities in Teeth", IEEE Journal of Translational Engineering in Health and Medicine, Dental, Oral, and Maxillofacial Medicine, vol. 5, 2017, pp. 1-7 (Year: 2017).*

* cited by examiner

MULTIWAVE DENTAL IMAGING SYSTEM

CROSS-REFERENCE TO RELATED APPLICATIONS

The present application claims priority to U.S. Provisional Patent Application Ser. No. 62/799,920, filed Feb. 1, 2019, which is hereby incorporated by reference in its entirety.

TECHNICAL BACKGROUND

The subject matter disclosed herein generally relates to the processing of data. Specifically, the present disclosure addresses systems and methods for processing multiple images generated at different optical wavelengths.

BACKGROUND

Current dental imaging technique require expensive equipment and time-consuming processes to identify tooth structure and caries properties. There is a need to provide accurate diagnostic information (that dictate appropriate treatment options given established clinical criteria) with less prohibitive cost.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Example methods and systems are directed to a method for multi-wave dental imaging. In one example embodiment, the present application describes a single pixel camera used in conjunction with an array of photodiodes (or a high speed spectrometer) to produce data streams used to simultaneously reconstruct multimodal images. In another example embodiment, the present application describes multiple cameras used in conjunction with a multi-wave light source. Each camera is configured to detect a predefined wavelength. The data stream from the cameras can be used to reconstruct multimodal images.

The present application describes a method to create a multimodal digital diagnostic map of a patient's oral dentition and surrounding gingival tissue using a digital micromirror device (DMD) single pixel camera. This method is intended for caries detection, but it can also be used for other types of dental/medical treatments by leveraging different wavelengths.

In one example embodiment, an imaging system comprises a first light source, a second light source, a beam combiner, an optical array sensor, and a computing device. The first light source forms a first beam of light at a first wavelength. The second light source forms a second beam of light at a second wavelength. The beam combiner combines the first beam of light and the second beam of light into a single beam of light and illuminates a specimen with the single beam of light. The optical array sensor detects reflected light that is reflected from the specimen. The computing device accesses sensor data from the optical array sensor, forms a first image based on the first wavelength and a second image based on the second wavelength, and forms a composite image from the first image and the second image. In one example embodiment, the image system comprises at least two light sources, each of different wavelengths.

In another example embodiment, a non-transitory machine-readable storage device may store a set of instructions that, when executed by at least one processor, causes the at least one processor to perform the method operations discussed within the present disclosure.

Examples merely typify possible variations. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

Figure 1:
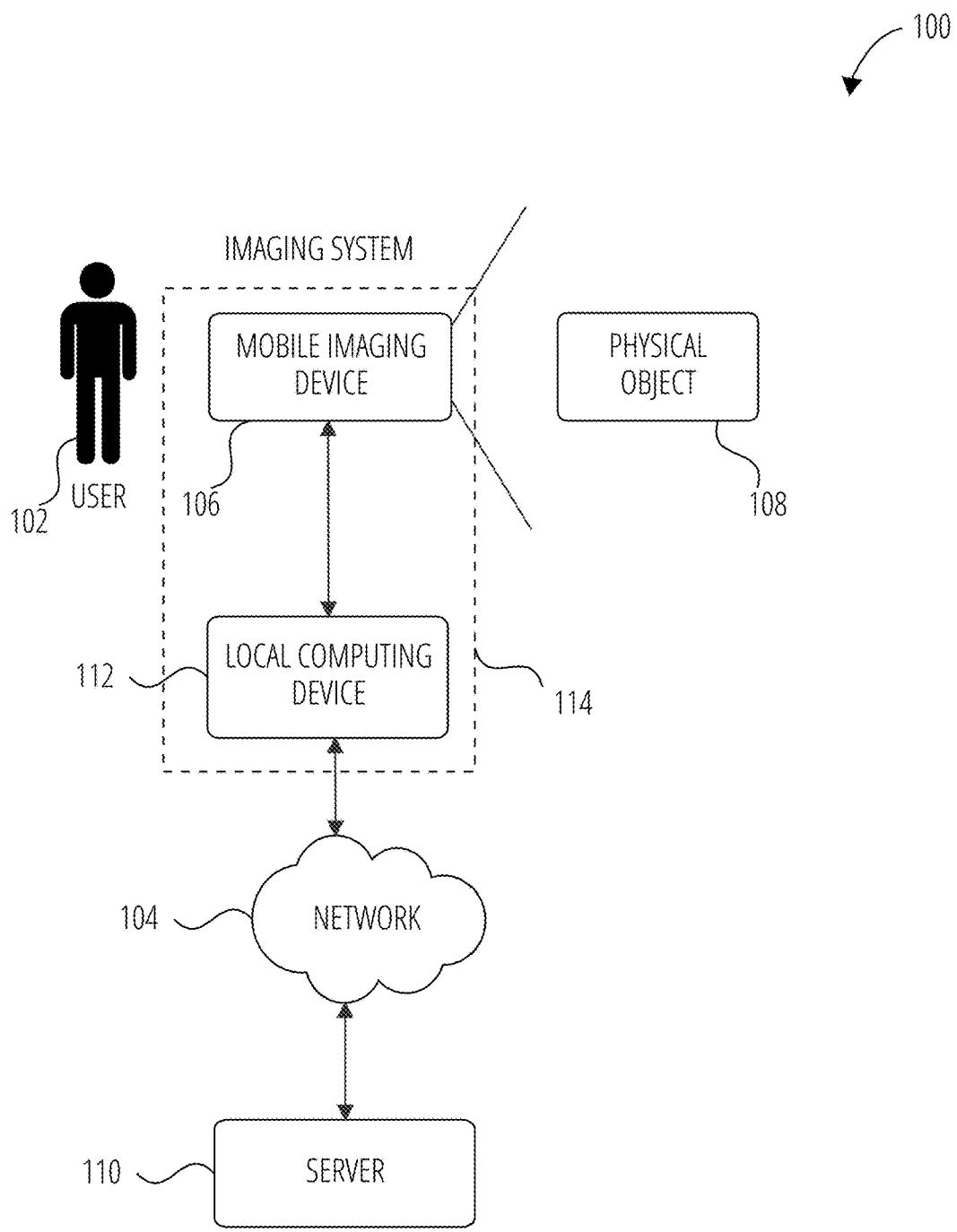
FIG. 1 illustrates a network environment for operating an imaging system in accordance with one example embodiment.

FIG. 1 is a network diagram illustrating a network environment 100 suitable for operating a mobile imaging device 106, according to some example embodiments. The network environment 100 includes an imaging system 114 and a server 110, communicatively coupled to each other via a network 104. The imaging system 114 and the server 110 may each be implemented in a computer system, in whole or in part, as described below with respect to FIG. 13.

The server 110 may be part of a network-based system. For example, the network-based system may be or include a cloud-based server system that provides additional information, such as three-dimensional models of specimens, to the mobile imaging device 106.

FIG. 1 illustrates a user 102 using the imaging system 114. The user 102 may be a human user (e.g., a human being), a machine user (e.g., a computer configured by a software program to interact with the mobile imaging device 106), or any suitable combination thereof (e.g., a human assisted by a machine or a machine supervised by a human). The user 102 is not part of the network environment 100, but is associated with the imaging system 114 and may be a user 102 of the imaging system 114.

The imaging system 114 includes a mobile imaging device 106 and a local computing device 112. The mobile imaging device 106 may include an image capturing device that is configured to illuminate the physical object 108 (e.g., a specimen such as a tooth) at different wavelengths (e.g., visible light range, 900 nm range, and 1450 nm range) and detect light reflected from the physical object 108.

The local computing device 112 may be a computing device with a display such as a smartphone, a tablet computer, or a laptop computer. The user 102 may be a user of an application in the local computing device 112. The application may include an imaging application configured to detect and identify a region of interest (e.g., cavities) at the physical object 108 and provide a visualization of the region of interest (e.g., indicated in a multi-wave reconstructed composite image) to the user 102.

The mobile imaging device 106 is capable of tracking its relative position and orientation in space. For example, the mobile imaging device 106 includes optical sensors (e.g., depth-enabled 3D camera, image camera), inertial sensors (e.g., gyroscope, accelerometer), wireless sensors (Bluetooth, Wi-Fi), and GPS sensor, to determine the location of the mobile imaging device 106 within a real world environment. The mobile imaging device 106 is described further below with respect to FIG. 2.

Any of the machines, databases, or devices shown in FIG. 1 may be implemented in a general-purpose computer modified (e.g., configured or programmed) by software to be a special-purpose computer to perform one or more of the functions described herein for that machine, database, or device. For example, a computer system able to implement any one or more of the methodologies described herein is discussed below with respect to FIG. 9 to FIG. 11. As used herein, a "database" is a data storage resource and may store data structured as a text file, a table, a spreadsheet, a relational database (e.g., an object-relational database), a triple store, a hierarchical data store, or any suitable combination thereof. Moreover, any two or more of the machines, databases, or devices illustrated in FIG. 1 may be combined into a single machine, and the functions described herein for any single machine, database, or device may be subdivided among multiple machines, databases, or devices.

The network 104 may be any network that enables communication between or among machines (e.g., server 110), databases, and devices (e.g., mobile imaging device 106). Accordingly, the network 104 may be a wired network, a wireless network (e.g., a mobile or cellular network), or any suitable combination thereof. The network 104 may include one or more portions that constitute a private network, a public network (e.g., the Internet), or any suitable combination thereof.

Figure 2:
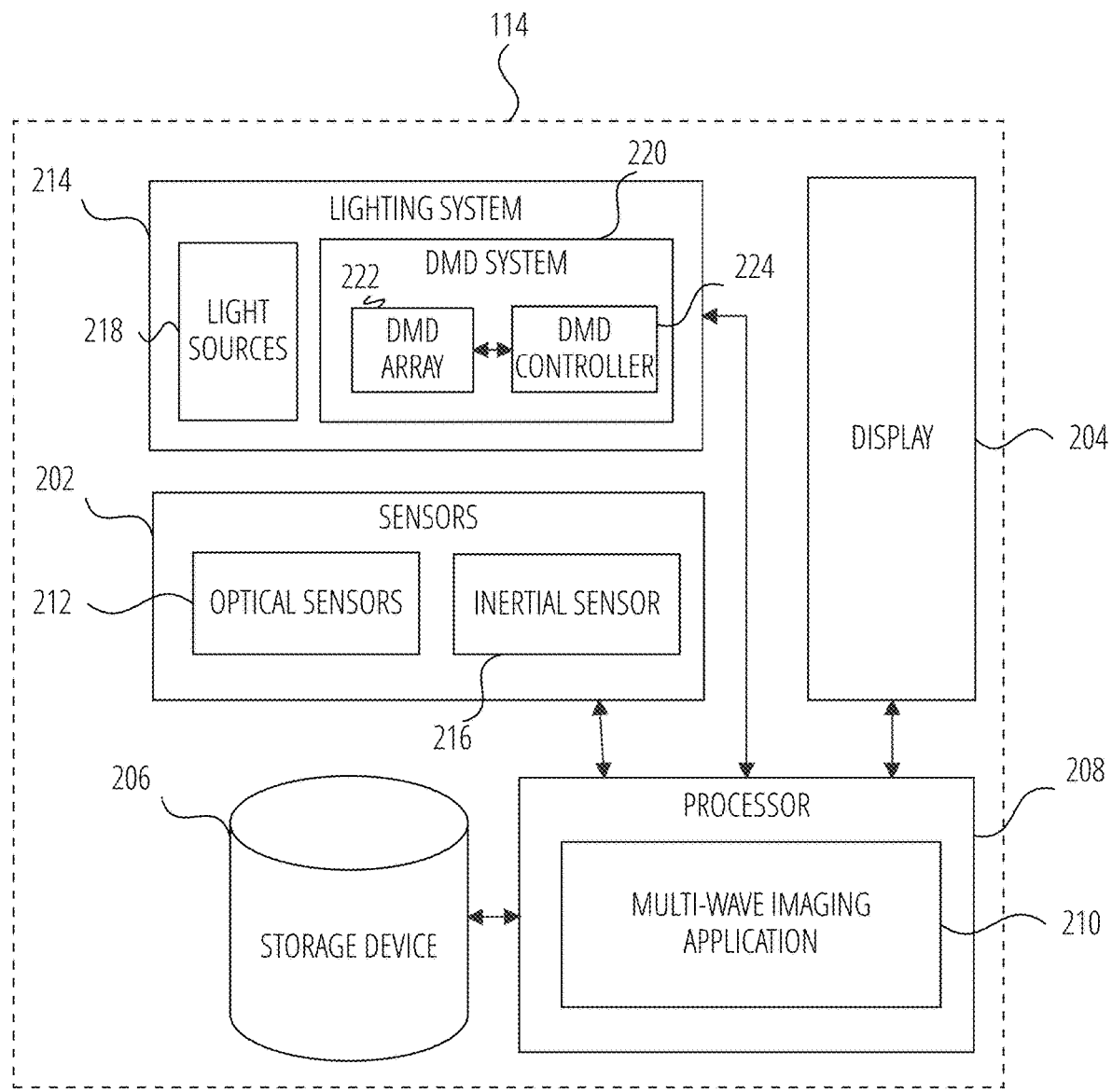
FIG. 2 illustrates an imaging system in accordance with one example embodiment.

FIG. 2 is a block diagram illustrating modules (e.g., components) of the imaging system 114, according to some example embodiments. The imaging system 114 comprises sensors 202, a display 204, a storage device 206, a processor 208, a multi-wave imaging application 210, an optical sensors 212, a lighting system 214, an inertial sensor 216, a light sources 218, and a DMD system 220.

The lighting system 214 includes light sources 218 and DMD system 220. The light sources 218 generate light at different spectral ranges (e.g., visible light range, 900 nm range, and 1450 nm range). In one example embodiment, the light sources 218 combines the light (e.g., light beam) from the different light sources 218 into a single beam and directs the single beam towards to the DMD system 220. The DMD system 220 includes a DMD array 222 and a DMD controller 224. The DMD controller 224 controls the DMD array 222 to project a pattern onto the physical object 108.

The sensors 202 include optical sensors 212 and an inertial sensor 216. The optical sensors 212 is configured to detect light reflected from the physical object 108. In one example, the optical sensors 212 include a photodiode array. In another example, the optical sensors 212 include multiple two-dimensional photo arrays sensor. Each sensor is configured to detect a predefined spectral range via a corresponding wavelength selective mirror.

The inertial sensor 216 includes, for example, a gyroscope or an accelerometer.

The processor 208 includes a multi-wave imaging application 210. The multi-wave imaging application 210 is configured to control the lighting system 214 and access sensor data from sensors 202. The multi-wave imaging application 210 generates an image for each wavelength based on the data steam from the sensors 202. The multi-wave imaging application 210 analyzes an image (corresponding to a predefined wavelength), detects and identifies a region of interest (e.g., carries) in the image obtained at the predefined wavelength. The multi-wave imaging application 210 generates a composite image based on the different wavelength images. The composite image includes a visual indication of the region of the interest.

In one example embodiment, the imaging system 114 may communicate over the network 104 with the server 110 to retrieve a portion of a database of visual references (e.g., images from different specimens).

Any one or more of the modules described herein may be implemented using hardware (e.g., a processor of a machine) or a combination of hardware and software. For example, any module described herein may configure a processor to perform the operations described herein for that module. Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices.

Figure 3:
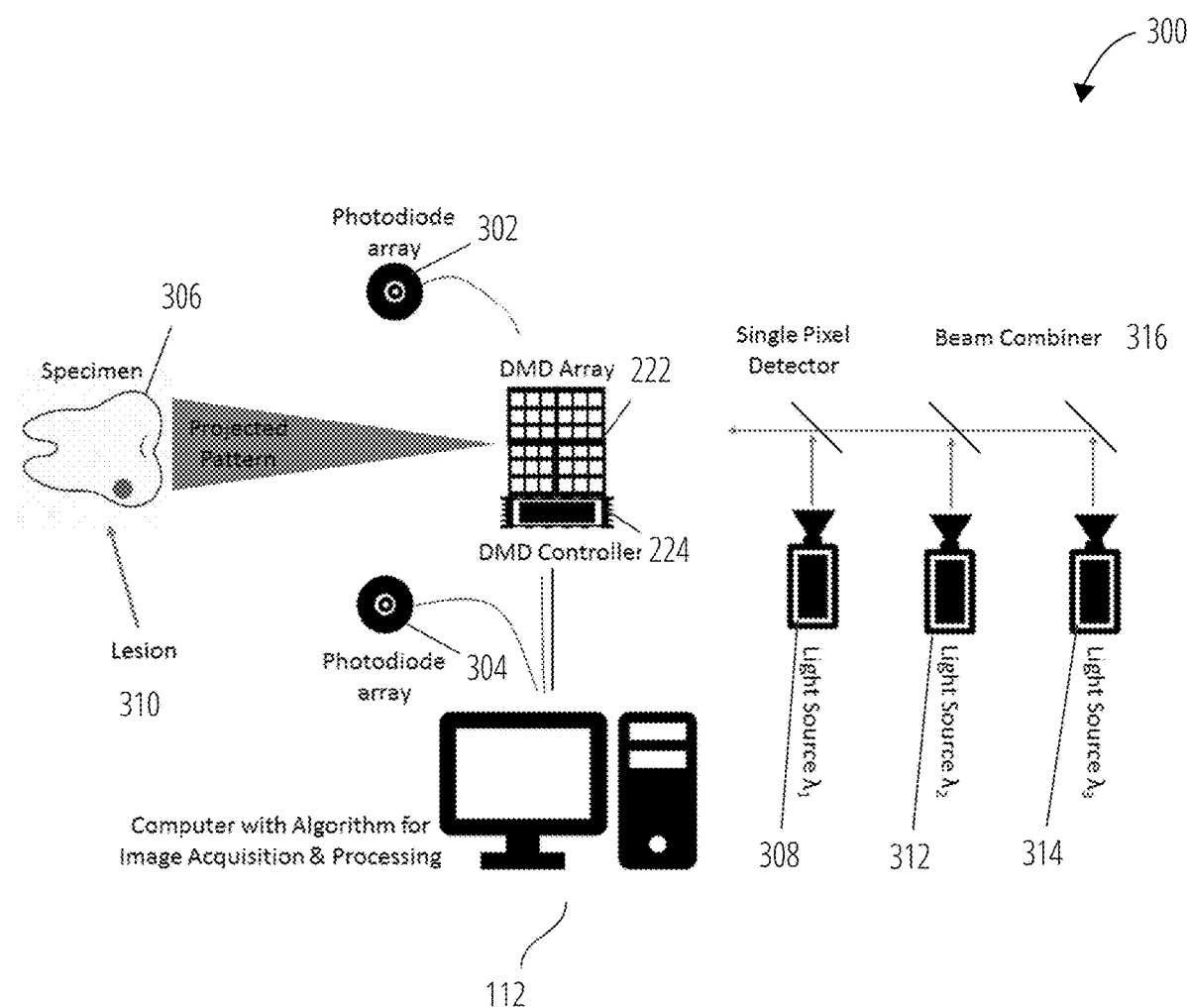
FIG. 3 illustrates an example operation of the imaging system in accordance with one embodiment.

FIG. 3 illustrates an example operation of an imaging system 300 in accordance with one embodiment. The imaging system 300 comprises a DMD array 222, a DMD controller 224, a photodiode array 302, a photodiode array 304, a specimen 306, a light source lambda1 308, a lesion 310, a light source lambda2 312, a light source lambda3 314, a beam combiner 316, and the local computing device 112. In the present embodiment, light of different wavelengths are combined and reflected from the DMD array to the specimen in a known projected pattern. Light reflected from the specimen is captured by photodiode arrays and reconstructed into a composite image on a computer. FIG. 3 illustrates three light sources. Other example embodiments include two or more light sources, where each light source generates a light in a different wavelength range.

The light sources (one or more wavelengths) are directed at the specimen 306 (e.g., tooth). The light source lambda1

308 generates a wavelength in the human-visible light spectrum, for example, of about 380 nm to about 740 nm to provide tooth surface information. Light source lambda2 312 generates a wavelength within the infrared spectrum, for example, of about 700 nm to about 1 mm to provide caries and dentin surface information. Light source lambda3 314 generates a wavelength also within the infrared spectrum, for example, of about 700 nm to 1 mm to provide caries information. In another example embodiment, 2500 nm can be used instead of 1 mm for light source lambda3 314.

The light beams from light source lambda1 308, light source lambda2 312, light source lambda3 314 are combined using a beam combiner 316 (e.g., partially transparent mirrors) to generate a single beam. In one example, polarizers filter the single beam and reduce specular reflectance. The single beam is directed towards the DMD array 222.

The local computing device 112 controls the DMD array 222 via the DMD controller 224. The DMD contains an array of small individually controlled mirrors. The DMD array 222 directs a projected pattern at the specimen 306. In one example, the DMD array 222 sequentially projects light onto the specimen 306.

The photodiode array 304 detect light reflected from the specimen 306. The photodiode array 304 consist of one or more photodiodes. One or more photodiodes corresponds to a different wavelength. The photodiode array 302 and photodiode array 304 are placed at predefined locations relative to the DMD array 222 (and/or the light source lambda1 308, light source lambda2 312, and light source lambda3 314).

The local computing device 112 accesses the analog data stream combined with the timing information sent to the DMD controller 224. The local computing device 112 reconstructs an image for each light source based on the timing information. For example, at t1, the local computing device 112 determines that the light captured at photodiode array 302 is based on light source lambda1 308. At t1+delta1, the local computing device 112 determines that the light captured at photodiode array 302 is based on light source lambda2 312. At t1+delta2, the local computing device 112 determines that the light captured at photodiode array 302 is based on light source lambda3 314. The local computing device 112 provides the timing information (e.g., t1, delta1, delta2) to the DMD controller 224.

The local computing device 112 generates a composite image that combines the images based on each light source (e.g., light source lambda1 308, light source lambda2 312, light source lambda3 314). The local computing device 112 identifies a lesion 310 on the image based on one of the light sources. The local computing device 112 indicates the lesion 310 in the composite image. The composite image registers a same pixel location in the composite image for each image based on each light source. For example, a pixel in a first image corresponds to a same pixel location in a second image. In other words, the images superimpose one another and are a direct location match to each other. There is no need to shift or transpose one image onto another to match them.

It is noted that the DMD array 222, corresponding DMD controller 224, and a single photodiode (e.g., light sources 218) are significantly cheaper than equivalent sensor arrays that are used in cameras for near infrared (NIR) wavelengths.

Figure 4:
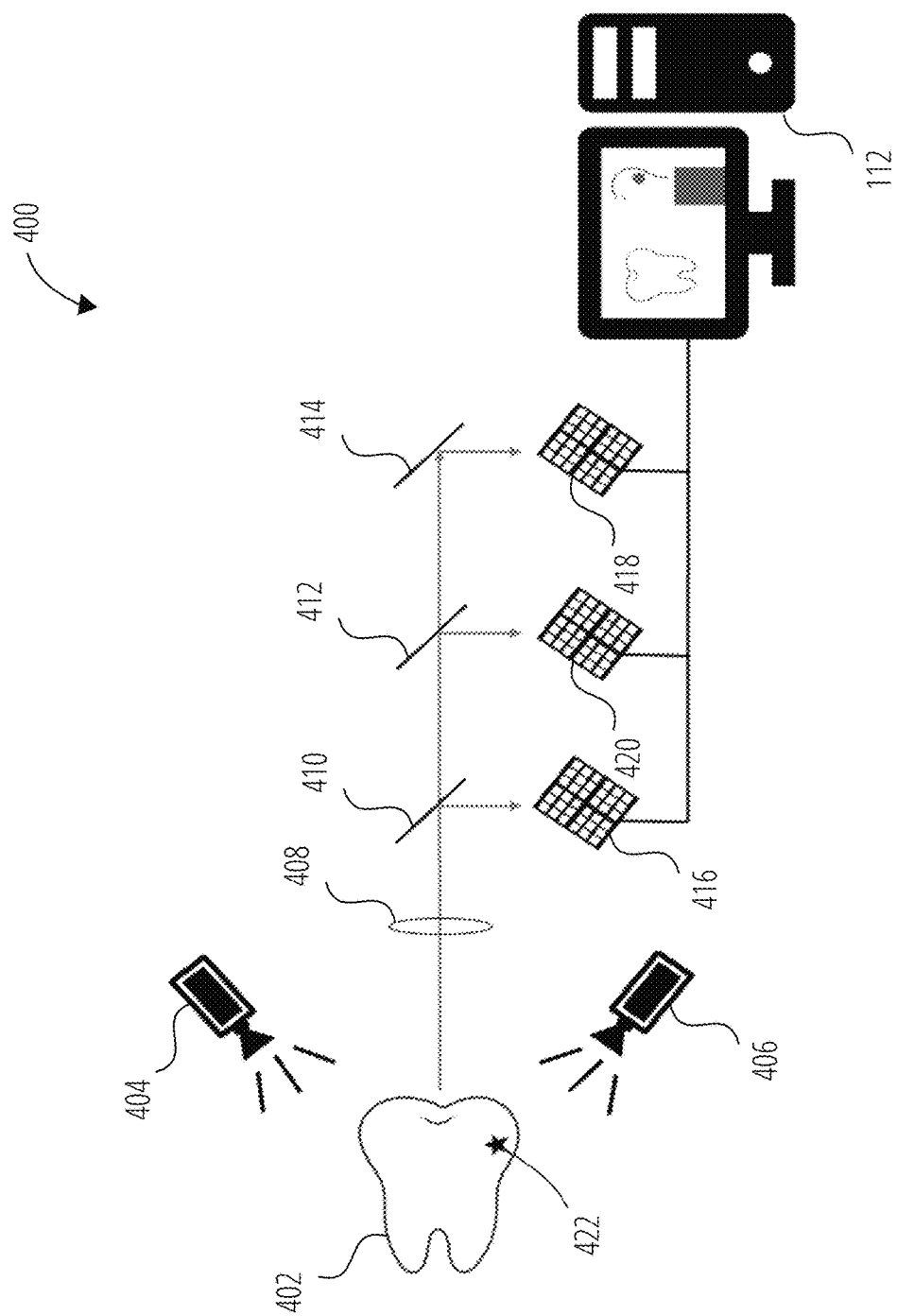
FIG. 4 illustrates an example operation of another imaging system in accordance with another example embodiment.

FIG. 4 illustrates an example operation of an imaging system in accordance with another example embodiment. The imaging system 400 comprises a specimen 402, a multispectral light source 404, a multispectral light source 406, a lens 408, a mirror 410, a mirror 412, a mirror 414, a 2D photo array 416, a 2D photo array 418, and a 2D photo array 420. In the present embodiment, multispectral light is reflected off of a specimen, separated via wavelength selective mirrors, projected into wavelength-specific 2D photo sensors, and reconstructed into a composite image on the computer.

The multispectral light source 404 and multispectral light source 406 (from human-visible light to infrared light) are directed at the specimen 402 (e.g., tooth). The lens 408 combines lights reflected from the specimen 402. The lens 408 can include an optical filter with different aperture and/or a polarizer. The lens 408 combine the reflected light into a single beam of light.

The single beam of light is directed at several mirrors (e.g., mirror 410, mirror 412, mirror 414). Each mirror may include a partially transparent mirror that filters the reflected light at a predefined wavelength range (e.g., mirror 410 may filter the single beam of light for visible light spectrum, mirror 412 may filter the single beam of light for infrared light spectrum). Each mirror is directed to reflect the filtered light to a corresponding photo array (e.g., mirror 410 reflects filtered light to 2D photo array 416, mirror 412 reflects filtered light to 2D photo array 420, mirror 414 reflects filtered light to 2D photo array 418). Each photo array is configured to detect light at a wavelength corresponding to the mirror.

The multi-wave imaging application 210 accesses the data stream from the 2D photo array 416, 2D photo array 420, and 2D photo array 418. The multi-wave imaging application 210 generates an image based on the sensor data from each photo array. For example, the multi-wave imaging application 210 generates a first image based on the sensor data from 2D photo array 416. The multi-wave imaging application 210 generates a second image based on the sensor data from 2D photo array 420. The multi-wave imaging application 210 generates a third image based on the sensor data from 2D photo array 418.

In one example embodiment, the multi-wave imaging application 210 generates a composite image that combines the first, second, and third images. The multi-wave imaging application 210 identifies a lesion 310 in one of the images based on its corresponding light source. The multi-wave imaging application 210 indicates the lesion 422 in the composite image. The composite image registers a same pixel location in the composite image for each image based on each light source.

Figure 5:
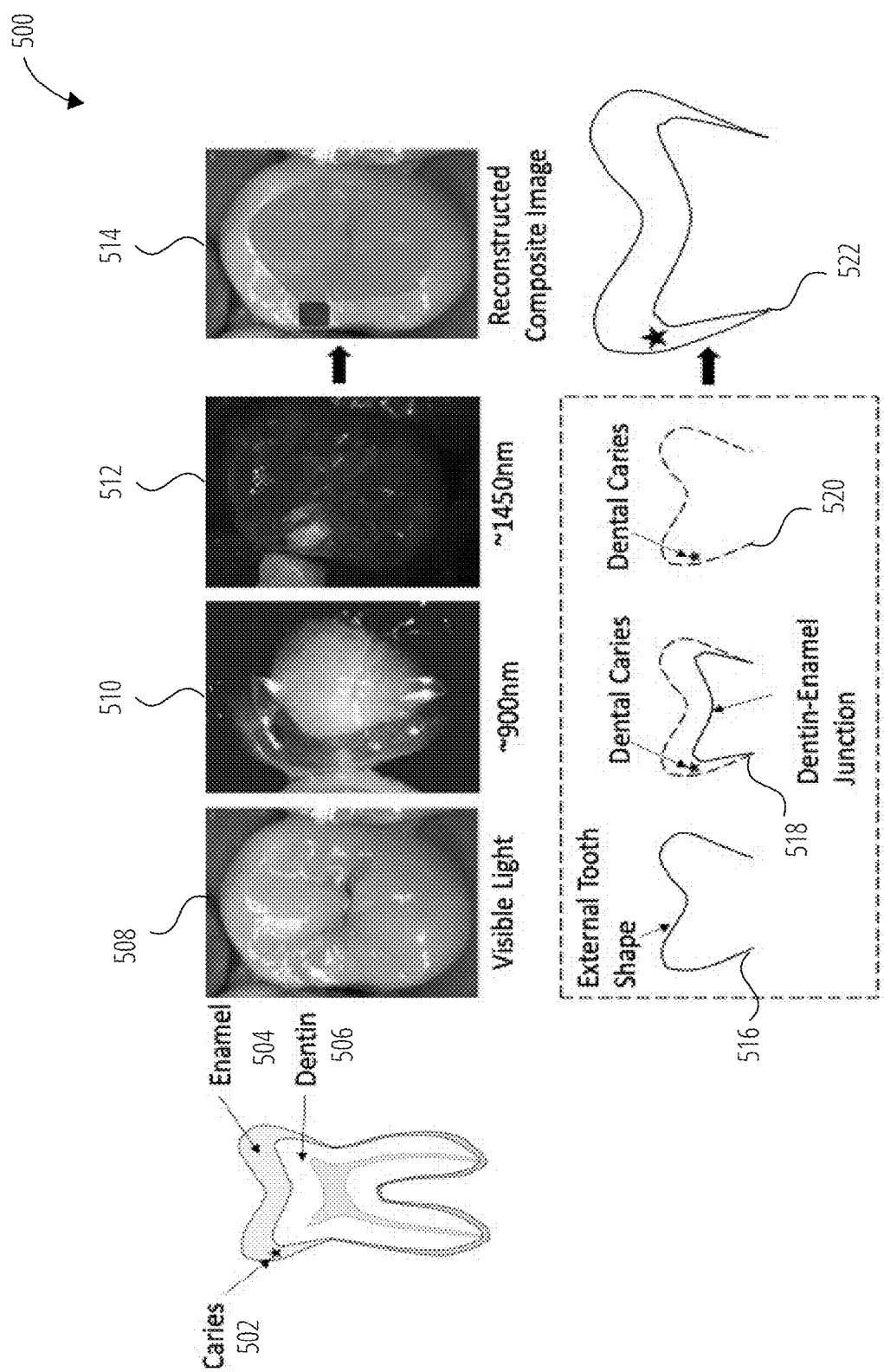
FIG. 5 illustrates an example of reconstructing a composite image in accordance with one example embodiment.

FIG. 5 illustrates an example of reconstructing a composite image in accordance with one example embodiment. The reconstruction process 500 comprises a caries 502, an enamel 504, a dentin 506, a visible light image 508, a 900 nm image 510, a 1450 nm image 512, a reconstructed composite image 514, an external tooth shape diagram 516, a dentin-enamel junction diagram 518, a dental caries diagram 520, and a reconstructed diagram 522.

Spectral information obtained from each photodiode is superimposed to reconstruct a composite image illustrating the external tooth shape, dentin-enamel junction, and dental caries. The reconstructed composite image 514 represents the visible light image augmented-with data extracted from the other wavelengths, specifically showing where the decay is in relationship to the dentin-enamel junction. The dental caries is detected in 1450 nm image 512 and dental caries diagram 520. The multi-wave imaging application 210 visually identifies/indicates the carries in the reconstructed composite image 514.

Figure 6:
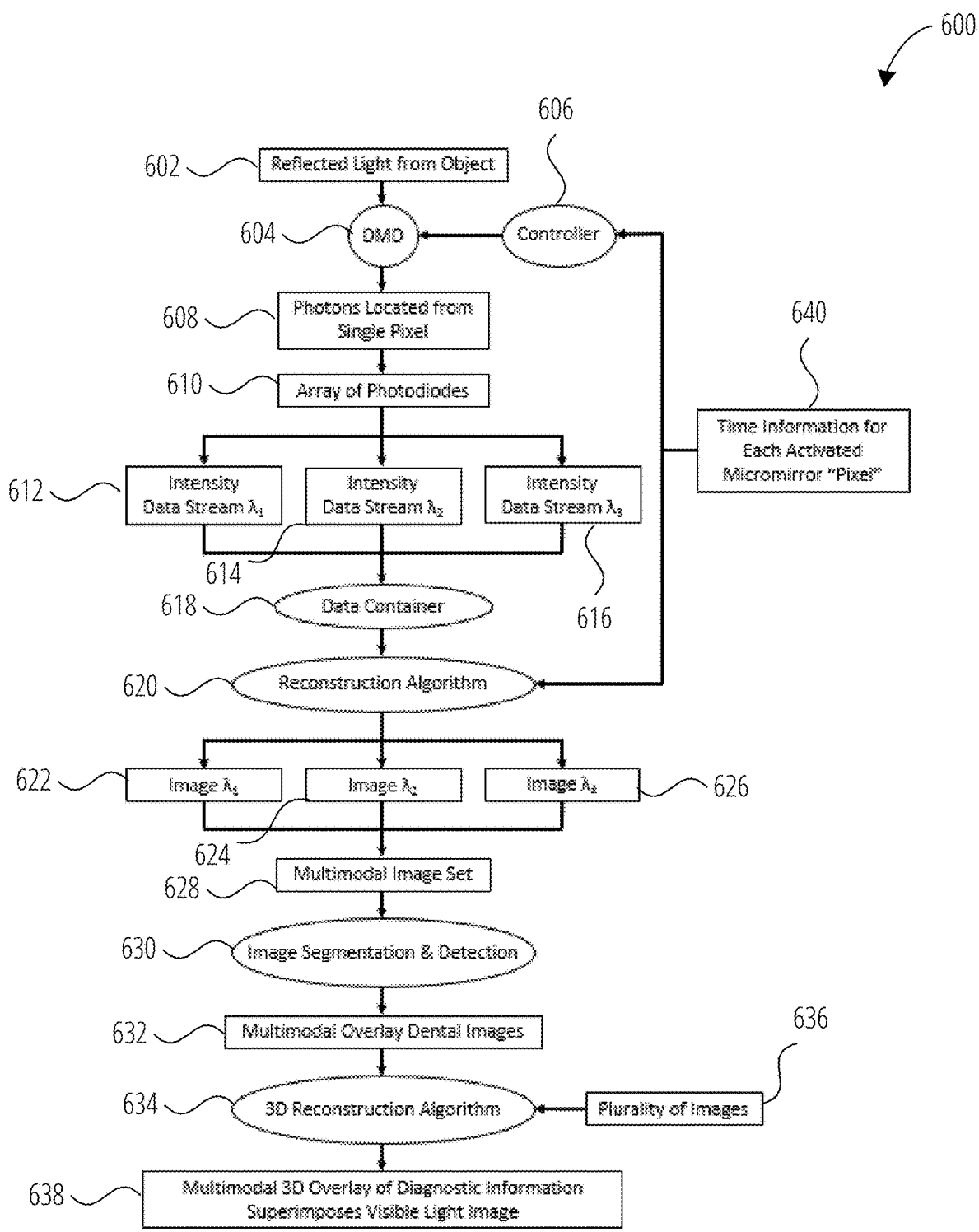
FIG. 6 is a flow diagram illustrating the path of image data acquisition using the present imaging system in accordance with one example embodiment.

FIG. 6 is a flow diagram illustrating a method 600 of the imaging system in accordance with one example embodiment. At operation 602, the reflected light from the physical object 108 is captured at the DMD array 604. The DMD controller 606 controls the direction of each mirrors in the DMD array 604 based on time information for each activated micromirror pixel 640. At operation 608, the photons (located from a single pixel) are detected in an array of photodiodes at operation 610. The photodiodes detect different data stream (each being based on a predefined wavelength): intensity data stream 612, intensity data stream 614, and intensity data stream 616.

A data container 618 stores the different data streams. In one example, the storage device 206 include the data container 618. A reconstruction algorithm 620 processes the different data streams. For example, the reconstruction algorithm 620 generates a first image 622 based on the intensity data stream 612, a second image 624 based on the intensity data stream 614, and a third image 626 based on the intensity data stream 616.

The reconstruction algorithm 620 combines the first image 622, second image 624, and third image 626 into a multimodal image set 628. In one example, image segmentation and detection 630 is performed on the multimodal image set 628 to identify regions of interest (e.g., carries). The different images are combined into a multimodal overlay dental images 632.

A 3D reconstruction algorithm 634 uses a plurality of images 636 to generate a 3D model at operation 638.

The following illustrates an example implementation of the method 600:

The imaging system simultaneously captures multiple images (2D or 3D) with identical (or substantially similar) perspectives (thus eliminating the need for registration steps) in multiple wavelengths. The structural/diagnostic data are extrapolated or identified from the multiple images with identical perspectives. The multiple images (with identical perspective) are integrated together to generate a composite image that is used to identify regions of interest within the composite image. In one example, the light source lambda1 308 uses wavelengths of 300 to 700 nm to generate tooth surface information. The light source lambda2 312 uses wavelengths from 701 nm to 1400 nm to generate caries and dentin surface information. The light source lambda3 314 uses wavelengths from 1401 nm to 1 mm to generate caries only information (if 1 mm is too big, can do 2500 nm).

In one example embodiment, the 2D images are taken sequentially use (on/off). In another example, embodiment, 3D images are generated based on multiple single-pixel detectors placed in different locations. Each single-pixel detector generates a 2D images. The 2D images are combined to produce a 3D image. For example, the surface gradient of a tooth can be generated based on the 2D images generated by the single-pixel detector placed at known distinct locations (different x and y directions). The surface gradients are integrated to reconstruct a 3D model of the tooth.

Incoming light from the specimen is sequentially projected in a predetermined pattern by the DMD onto a photodiode array: The simplest pattern is to activate each individual micro-mirror pixel directly onto the photodiode. Mathematical patterns can be used to approximate an image. Voltage(s) of the photodiode array indicating photon density over time is fed into the computer.

A reconstruction algorithm using the prior knowledge of the pattern creates an image for each photodiode wavelength: for reconstructed images, the analogous images taken at different wavelengths are registered.

The inherent registration of each image can lend itself to produce diagnostic overlays (e.g. overlay image). Segmentation techniques that identify caries (e.g. scattering intensity of reflected photons) can be overlaid with visible light images. Given a plurality of images, it is possible to generate a 3D overlay model of the tooth and the dental decay within.

Figure 7:
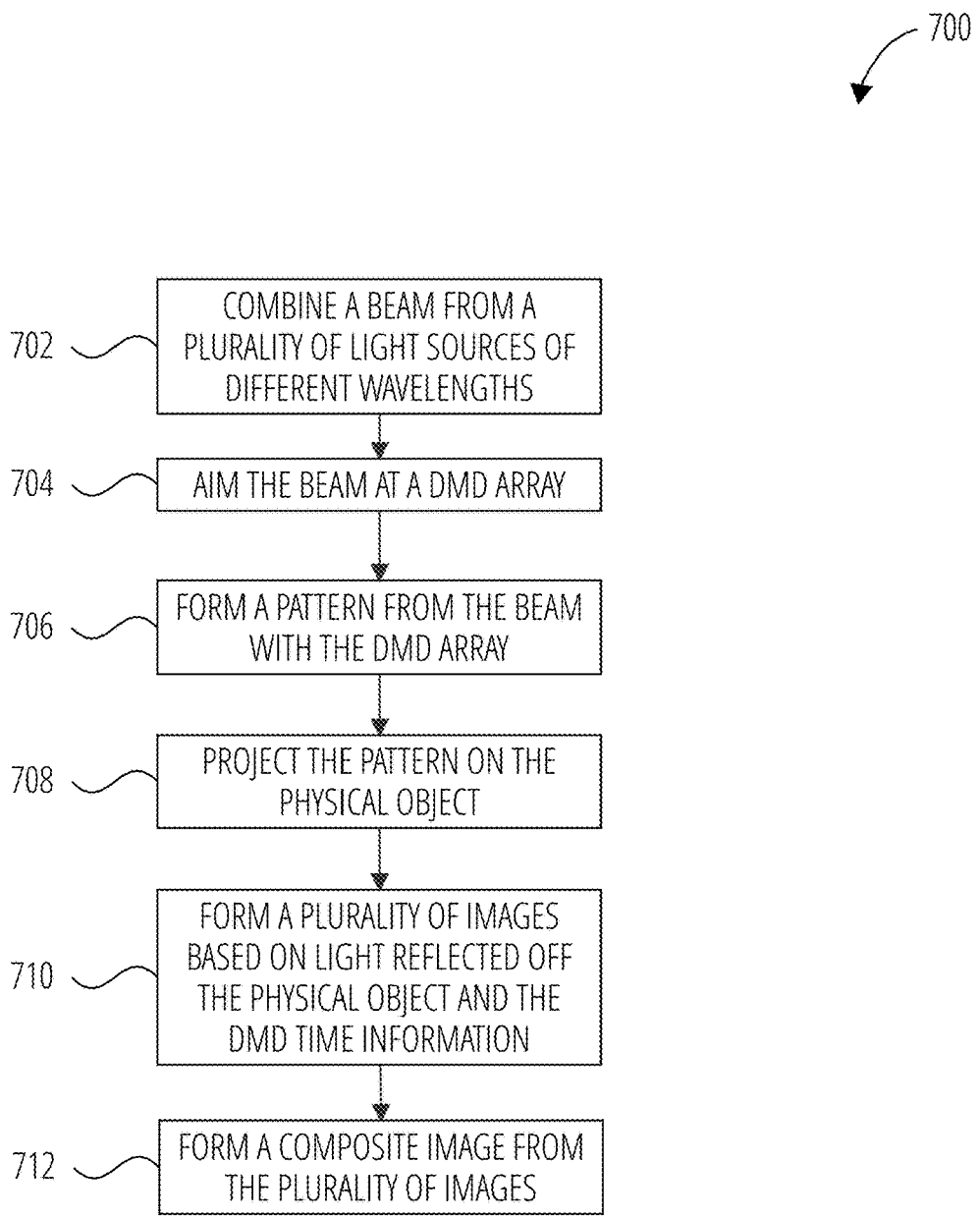
FIG. 7 is a flow diagram illustrating a method for forming a composite image in accordance with one example embodiment.

FIG. 7 is a flow diagram illustrating a method 700 for forming a composite image in accordance with one example embodiment. At block 702, the beam combiner 316 combines a beam from a plurality of light sources of different wavelengths. At block 704, the beam combiner 316 aims the beam at a DMD array 604. At block 706, the DMD array 222 forms a pattern from the beam. At block 708, the DMD array 222 projects the pattern on the physical object 108. At block 710, the photodiode array 302 detects light reflected off the physical object 108. The local computing device 112 forms images based on the data signal and the DMD time information. At block 712, the local computing device 112 forms a composite image from the plurality of images.

Figure 8:
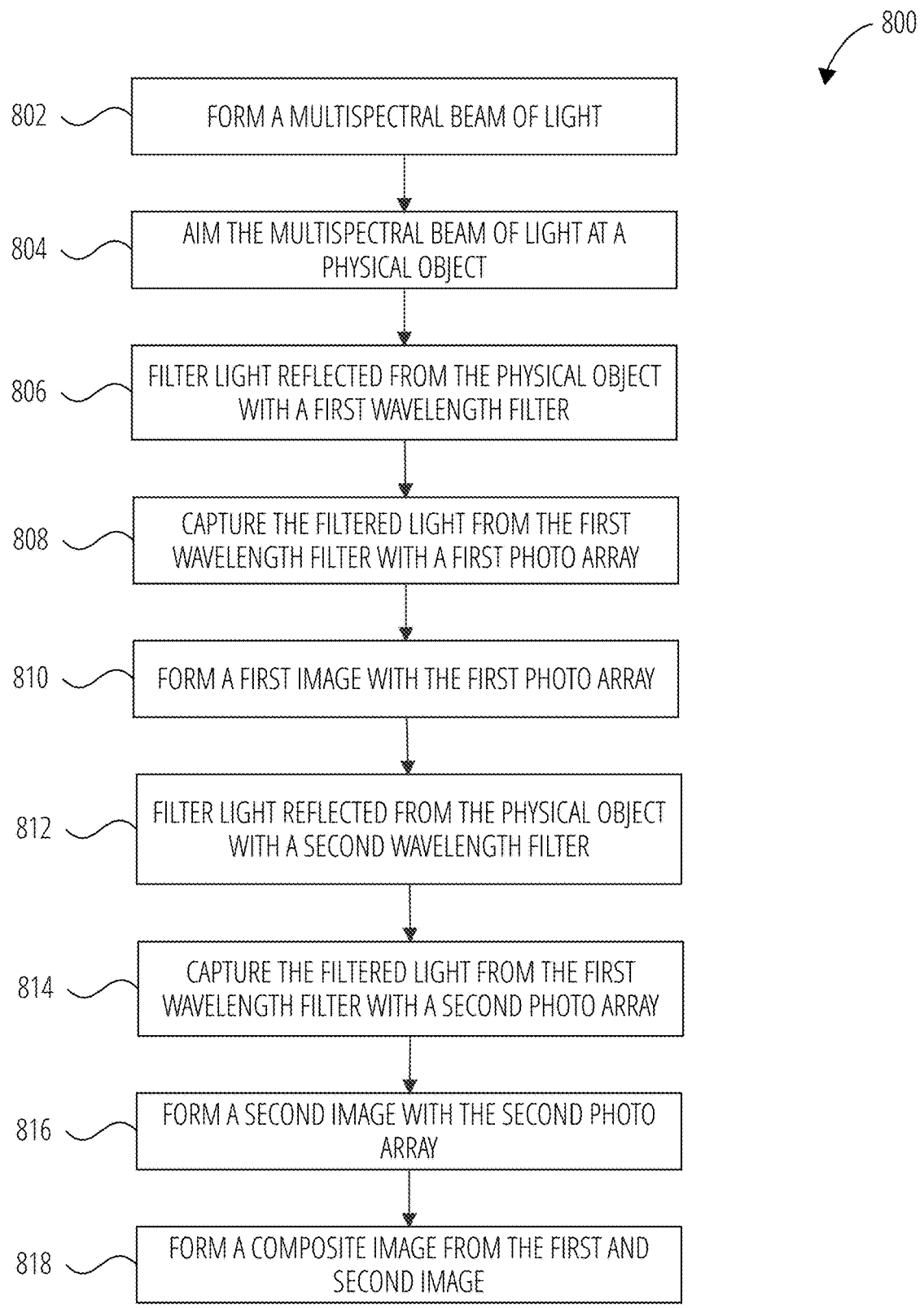
FIG. 8 is a flow diagram illustrating a method for forming a composite image in accordance with one example embodiment.

FIG. 8 is a flow diagram illustrating a method 800 for forming a composite image in accordance with one example embodiment. At block 802, a multispectral light source 404 (deleted) forms a multispectral beam of light. At block 804, the multispectral light source 404 (deleted) aims the multispectral beam of light at the specimen 402 (deleted). At block 806, the mirror 410 (deleted) filters light reflected from the specimen 402 (deleted). At block 808, the 2D photo array 416 (deleted) captures the filtered light from the mirror 410 (deleted). At block 810, the multi-wave imaging application 210 forms a first image with data from the 2D photo array 416 (deleted). At block 812, the mirror 412 (deleted) filters light reflected from the specimen 402 (deleted). At block 814, the 2D photo array 420 (deleted) captures the filtered light from the mirror 412 (deleted). At block 816, the multi-wave imaging application 210 forms a second image with data from the 2D photo array 420 (deleted). At block 818, the multi-wave imaging application 210 forms a composite image from the first and second image.

Figure 9:
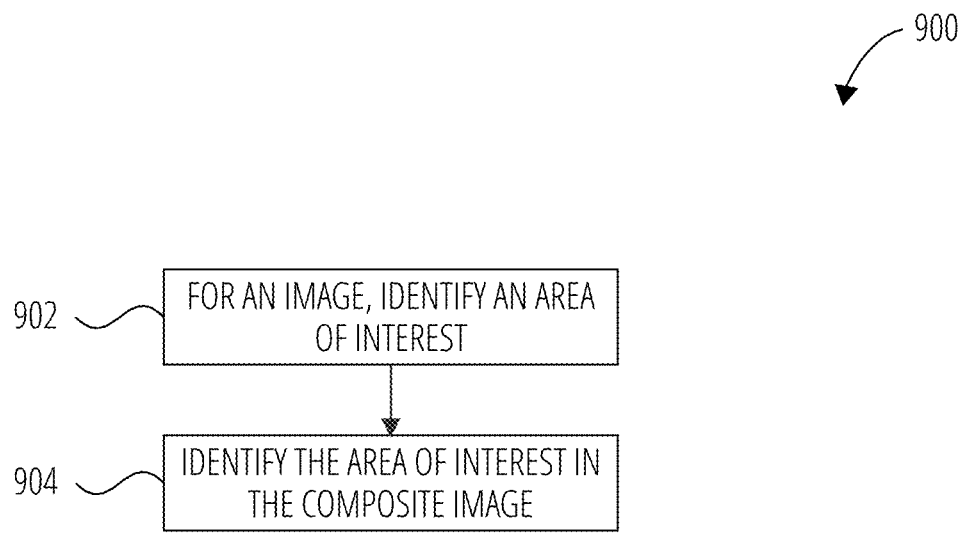
FIG. 9 is a flow diagram illustrating a method for identifying an area of interest in the composite image from images of different wavelengths.

FIG. 9 is a flow diagram illustrating a method 900 for identifying an area of interest in the composite image from images of different wavelengths. At block 902, the multi-wave imaging application 210 identifies an area of interest for an image corresponding to a particular wavelength. In one example, the multi-wave imaging application 210 detects regions of interest based on the predefined parameters or using a machine learning model. At block 904, the multi-wave imaging application 210 identifies the area of interest in the composite image based on the identified area of interest in one of the images.

Figure 10:
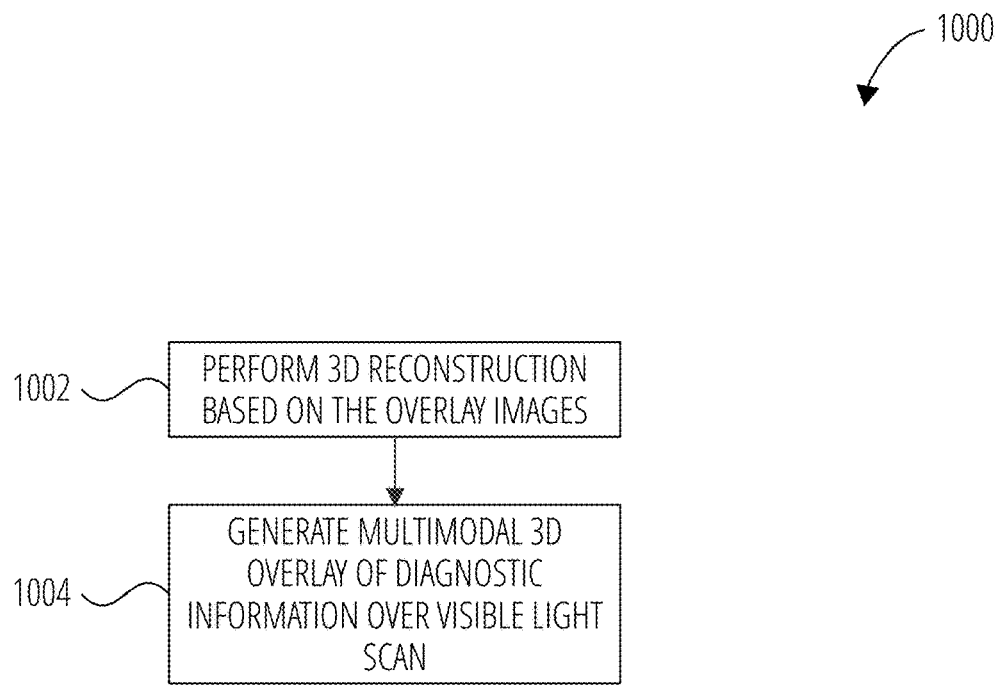
FIG. 10 is a flow diagram illustrating a method for generating a multimodal 3D overlay of diagnostic information in accordance with one example embodiment.

FIG. 10 is a flow diagram illustrating a method 1000 for generating a multimodal 3D overlay of diagnostic information in accordance with one example embodiment. At block 1002, the multi-wave imaging application 210 performs a 3D reconstruction based on the overlaid images. At block 1004, the multi-wave imaging application 210 generates a multi-model 3D overlay of diagnostic information over visible light scan.

Figure 11:
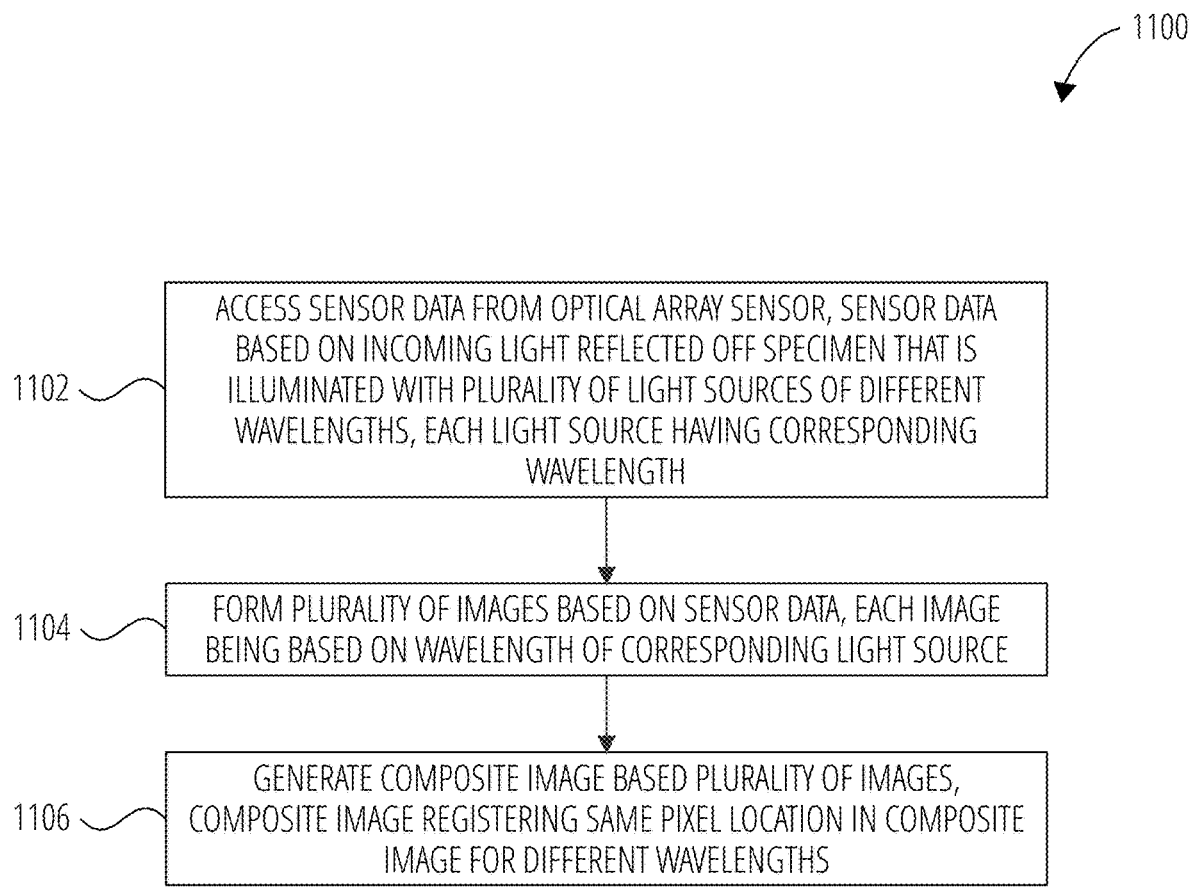
FIG. 11 illustrates a routine in accordance with one example embodiment.

FIG. 11 illustrates a routine in accordance with one example embodiment. In block 1102, routine 1100 accesses sensor data from an optical array sensor, the sensor data based on incoming light reflected off a specimen that is illuminated with a plurality of light sources of different wavelengths, each light source having a corresponding wavelength. In block 1104, routine 1100 forms a plurality of images based on the sensor data, each image being based on a wavelength of a corresponding light source. In block 1106, routine 1100 generates a composite image based the plurality of images, the composite image registering a same pixel location in the composite image for the different wavelengths.

Figure 12:
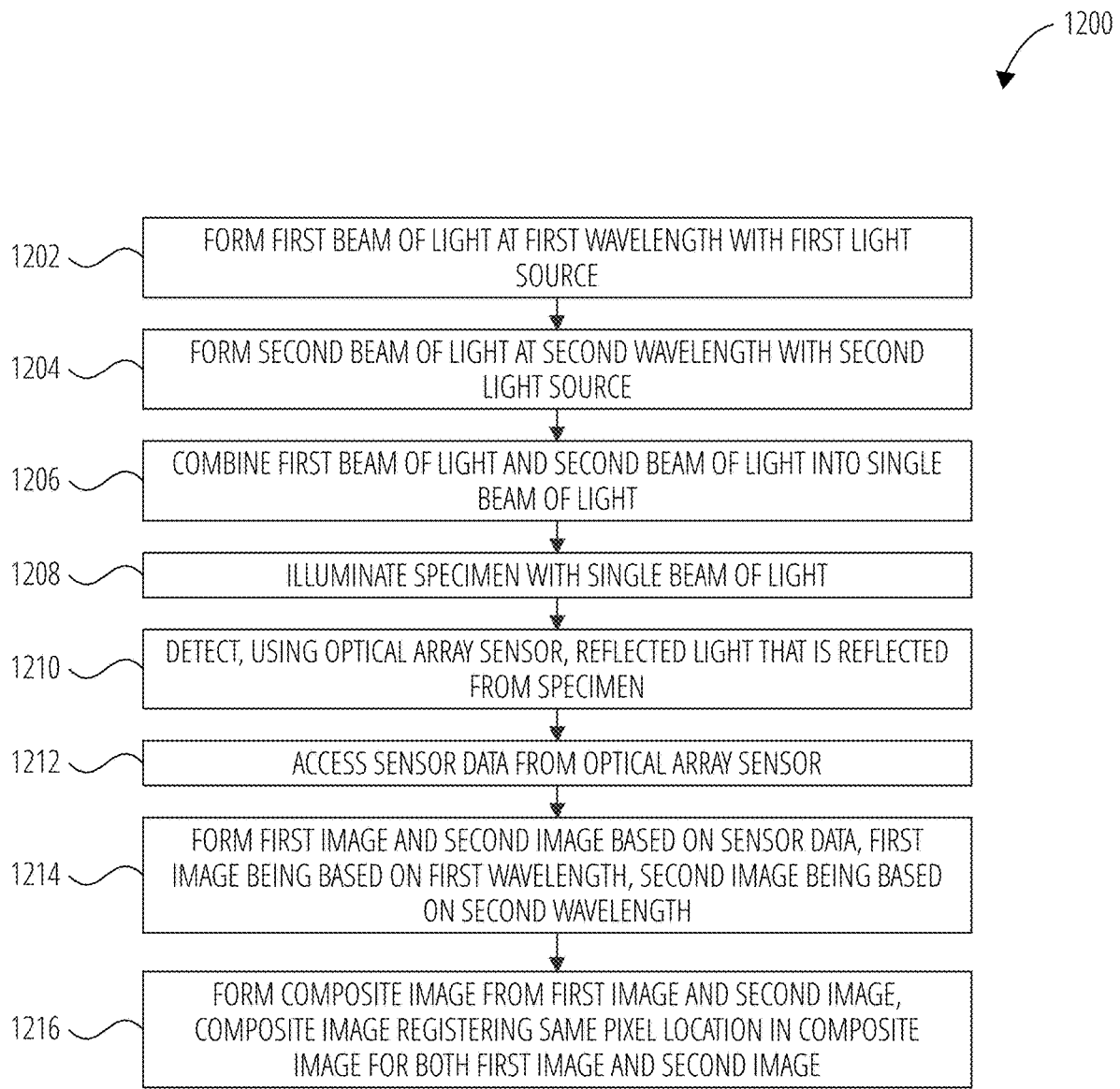
FIG. 12 illustrates a routine in accordance with one example embodiment.

FIG. 12 illustrates a routine in accordance with one example embodiment. In block 1202, routine 1200 forms a first beam of light at a first wavelength with a first light source. In block 1204, routine 1200 forms a second beam of light at a second wavelength with a second light source. In block 1206, routine 1200 combines the first beam of light and the second beam of light into a single beam of light. In block 1208, routine 1200 illuminates a specimen with the single beam of light. In block 1210, routine 1200 detects, using an optical array sensor, reflected light that is reflected from the specimen. In block 1212, routine 1200 accesses sensor data from the optical array sensor. In block 1214, routine 1200 forms a first image and a second image based on the sensor data, the first image being based on the first wavelength, the second image being based on the second wavelength. In block 1216, routine 1200 forms a composite image from the first image and the second image, the composite image registering a same pixel location in the composite image for both the first image and the second image.

Figure 13:
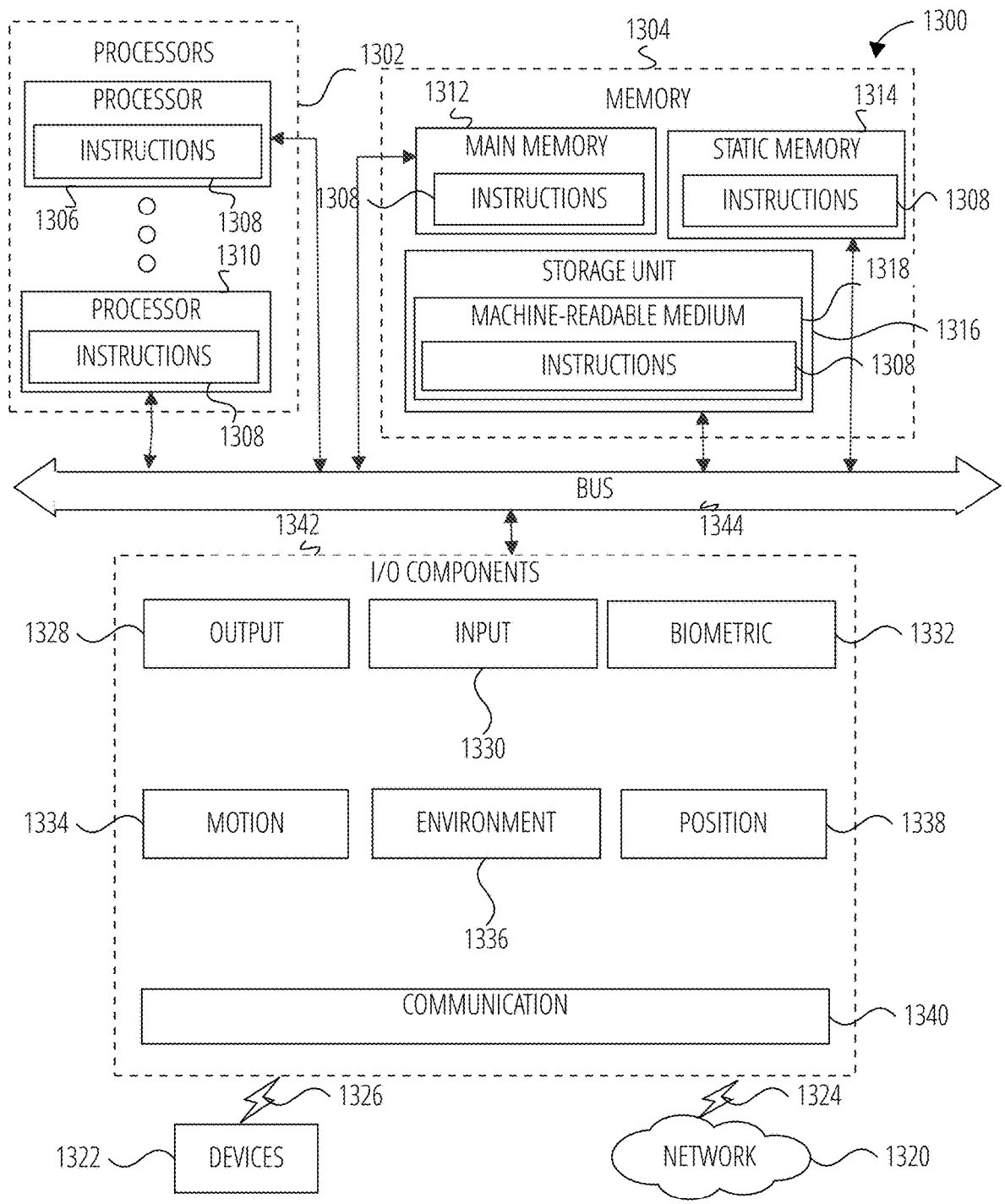
FIG. 13 is a diagrammatic representation of a machine in the form of a computer system within which a set of instructions may be executed for causing the machine to perform any one or more of the methodologies discussed herein, according to one example embodiment.

FIG. 13 is a diagrammatic representation of the machine 1300 within which instructions 1308 (e.g., software, a program, an application, an applet, an app, or other executable code) for causing the machine 1300 to perform any one or more of the methodologies discussed herein may be executed. For example, the instructions 1308 may cause the machine 1300 to execute any one or more of the methods described herein. The instructions 1308 transform the general, non-programmed machine 1300 into a particular machine 1300 programmed to carry out the described and illustrated functions in the manner described. The machine 1300 may operate as a standalone device or may be coupled (e.g., networked) to other machines. In a networked deployment, the machine 1300 may operate in the capacity of a server machine or a client machine in a server-client network environment, or as a peer machine in a peer-to-peer (or distributed) network environment. The machine 1300 may comprise, but not be limited to, a server computer, a client computer, a personal computer (PC), a tablet computer, a laptop computer, a netbook, a set-top box (STB), a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 1308, sequentially or otherwise, that specify actions to be taken by the machine 1300. Further, while only a single machine 1300 is illustrated, the term "machine" shall also be taken to include a collection of machines that individually or jointly execute the instructions 1308 to perform any one or more of the methodologies discussed herein.

The machine 1300 may include processors 1302, memory 1304, and I/O components 1342, which may be configured to communicate with each other via a bus 1344. In an example embodiment, the processors 1302 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an ASIC, a Radio-Frequency Integrated Circuit (RFIC), another Processor, or any suitable combination thereof) may include, for example, a Processor 1306 and a Processor 1310 that execute the instructions 1308. The term "Processor" is intended to include multi-core processors that may comprise two or more independent processors (sometimes referred to as "cores") that may execute instructions contemporaneously. Although FIG. 13 shows multiple processors 1302, the machine 1300 may include a single Processor with a single core, a single Processor with multiple cores (e.g., a multi-core Processor), multiple processors with a single core, multiple processors with multiples cores, or any combination thereof.

The memory 1304 includes a main memory 1312, a static memory 1314, and a storage unit 1316, both accessible to the processors 1302 via the bus 1344. The main memory 1304, the static memory 1314, and storage unit 1316 store the instructions 1308 embodying any one or more of the methodologies or functions described herein. The instructions 1308 may also reside, completely or partially, within the main memory 1312, within the static memory 1314, within machine-readable medium 1318 within the storage unit 1316, within at least one of the processors 1302 (e.g., within the Processor's cache memory), or any suitable combination thereof, during execution thereof by the machine 1300.

The I/O components 1342 may include a wide variety of components to receive input, provide output, produce output, transmit information, exchange information, capture measurements, and so on. The specific I/O components 1342 that are included in a particular machine will depend on the type of machine. For example, portable machines such as mobile phones may include a touch input device or other such input mechanisms, while a headless server machine will likely not include such a touch input device. It will be appreciated that the I/O components 1342 may include many other components that are not shown in FIG. 13. In various example embodiments, the I/O components 1342 may include output components 1328 and input components 1330. The output components 1328 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 1330 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 1342 may include biometric components 1332, motion components 1334, environmental components 1336, or position components 1338, among a wide array of other components. For example, the biometric components 1332 include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1334 include acceleration sensor components (e.g., accelerometer), gravitation sensor components, rotation sensor components (e.g., gyroscope), and so forth. The environmental components 1336 include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 1338 include location sensor components (e.g., a GPS receiver Component), altitude sensor components (e.g., altimeters or barometers that detect air pressure from which altitude may be derived), orientation sensor components (e.g., magnetometers), and the like.

Communication may be implemented using a wide variety of technologies. The I/O components 1342 further include communication components 1340 operable to couple the machine 1300 to a network 1320 or devices 1322 via a coupling 1324 and a coupling 1326, respectively. For example, the communication components 1340 may include a network interface Component or another suitable device to interface with the network 1320. In further examples, the communication components 1340 may include wired communication components, wireless communication components, cellular communication components, Near Field Communication (NFC) components, Bluetooth® components (e.g., Bluetooth® Low Energy), WiFi® components, and other communication components to provide communication via other modalities. The devices 1322 may be another machine or any of a wide variety of peripheral devices (e.g., a peripheral device coupled via a USB).

Moreover, the communication components 1340 may detect identifiers or include components operable to detect identifiers. For example, the communication components 1340 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1340, such as location via Internet Protocol (IP) geolocation, location via Wi-Fi® signal triangulation, location via detecting an NFC beacon signal that may indicate a particular location, and so forth.

The various memories (e.g., memory 1304, main memory 1312, static memory 1314, and/or memory of the processors 1302) and/or storage unit 1316 may store one or more sets of instructions and data structures (e.g., software) embodying or used by any one or more of the methodologies or functions described herein. These instructions (e.g., the instructions 1308), when executed by processors 1302, cause various operations to implement the disclosed embodiments.

The instructions 1308 may be transmitted or received over the network 1320, using a transmission medium, via a network interface device (e.g., a network interface Component included in the communication components 1340) and using any one of a number of well-known transfer protocols (e.g., hypertext transfer protocol (HTTP)). Similarly, the instructions 1308 may be transmitted or received using a transmission medium via the coupling 1326 (e.g., a peer-to-peer coupling) to the devices 1322.

Although an embodiment has been described with reference to specific example embodiments, it will be evident that various modifications and changes may be made to these embodiments without departing from the broader scope of the present disclosure. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

EXAMPLES

Example 1 includes a method comprising: forming a first beam of light at a first wavelength with a first light source; forming a second beam of light at a second wavelength with a second light source; combining the first beam of light and the second beam of light into a single beam of light; illuminating a specimen with the single beam of light; detecting, using an optical array sensor, reflected light that is reflected from the specimen; accessing sensor data from the optical array sensor; forming a first image and a second image based on the sensor data, the first image being based on the first wavelength, the second image being based on the second wavelength; and forming a composite image from the first image and the second image, the composite image registering a same pixel location in the composite image for both the first image and the second image.

Example 2 includes example 1, wherein illuminating the specimen further comprises: illuminating a digital micro-mirror device (DMD) array with the single beam of light, the single beam of light corresponding to a single pixel of the optical array sensor; controlling the DMD array with a DMD controller (to form a pattern of light); forming a pattern of light with the DMD controller, the pattern of light corresponding to an array of pixels; and projecting the pattern of light onto the specimen.

Example 3 includes any of the above examples, wherein a first sensor from the optical array sensor is configured to detect light at the first wavelength, wherein a second sensor from the optical array sensor is configured to detect light at the second wavelength.

Example 4 includes any of the above examples, wherein the specimen comprises a tooth, wherein the first wavelength comprises human-visible light wavelength, wherein the second wavelength is at 900 nm or 1450 nm.

Example 5 includes any of the above examples, further comprising: identifying dental caries in the second image; and indicating the dental caries in the composite image.

Example 6 includes any of the above examples, further comprising: generating a first plurality of images based on the first wavelength; generating a second plurality of images based on the second wavelength; and generating a three-dimensional model of the specimen based on the first and second plurality of images.

Example 7 includes any of the above examples, further comprising: identifying a region of interest in the second image; and indicating the region of interest in the composite image.

Example 8 includes an imaging system comprising: a first light source configured to form a first beam of light at a first wavelength; a second light source configured to form a second beam of light at a second wavelength; a beam combiner configured to combine the first beam of light and the second beam of light into a single beam of light and to illuminate a specimen with the single beam of light; an optical array sensor configured to detect reflected light that is reflected from the specimen; and a computing device coupled to the optical array sensor and configured to: access sensor data from the optical array sensor; form a first image and a second image based on the sensor data, the first image being based on the first wavelength, the second image being based on the second wavelength; and form a composite image from the first image and the second image, the composite image registering a same pixel location in the composite image for both the first image and the second image.

Example 9 includes any of the above examples, further comprising: a digital micro-mirror device (DMD) array configured to illuminate the specimen with the single beam of light, the single beam of light corresponding to a single pixel of the optical array sensor; and a DMD controller configured to control the DMD array, to form a pattern of light, the pattern of light corresponding to an array of pixels, and to project the pattern of light onto the specimen.

Example 10 includes any of the above examples, wherein a first sensor from the optical array sensor is configured to detect light at the first wavelength, wherein the second sensor from the optical array sensor is configured to detect light at the second wavelength.

Example 11 includes any of the above examples, wherein the specimen comprises a tooth, wherein the first wavelength comprises human-visible light wavelength, wherein the second wavelength is at 900 nm or 1450 nm.

Example 12 includes any of the above examples, wherein the computing device is further configured to: identify dental caries in the second image; and indicate the dental caries in the composite image.

Example 13 includes any of the above examples, wherein the computing device is further configured to: generate a first plurality of images based on the first wavelength; generate a second plurality of images based on the second wavelength; and generate a three-dimensional model of the specimen based on the first and second plurality of images.

Example 14 includes any of the above examples, wherein the instructions further configure the apparatus to: identify a region of interest in the second image; and indicate the region of interest in the composite image.

Example 15 includes an imaging system comprising: a multi-spectrum light source configured to form and direct a beam of light at multiple wavelengths at a specimen; a beam combiner that combines reflected light from the specimen into a single beam of light; a first optical filter configured to filter the single beam of light at a first wavelength; a second optical filter configured to filter the single beam of light at a second wavelength; a first array sensor configured to detect the filtered single beam of light at the first wavelength from the first optical filter; a second array sensor configured to detect the filtered single beam of light at the second wavelength from the second optical filter; a computing device coupled to the first and second array sensor configured to: access first sensor data from the first array sensor; access second sensor data from the second array sensor; form a first image based on the first sensor data, the first image corresponding to the first wavelength; form a second image based on the second sensor data, the second image corresponding to the second wavelength; and form a composite image from the first image and the second image, the composite image registering a same pixel location in the composite image for both the first image and the second image.

Example 16 includes any of the above examples, wherein the specimen comprises a tooth, wherein the first wavelength comprises human-visible light wavelength, wherein the second wavelength is at 900 nm or 1450 nm.

Example 17 includes any of the above examples, wherein the computing device is further configured to: identify dental caries in the second image; and indicate the dental caries in the composite image.

Example 18 includes any of the above examples, wherein the computing device is further configured to: generate a first plurality of images based on the first wavelength; generate a second plurality of images based on the second wavelength; and generate a three-dimensional model of the specimen based on the first and second plurality of images.

Example 19 includes any of the above examples, wherein the beam combiner comprises an optical lens, wherein the first array sensor comprises a first two-dimensional optical sensor, wherein the second array sensor comprises a second two-dimensional optical sensor.

Example 20 includes any of the above examples, wherein the first optical filter comprises a first semi-transparent mirror that filters every wavelengths except for the first wavelength, wherein the second optical filter comprises a second semi-transparent mirror that filters wavelengths based on the first wavelength.

What is claimed is:

1. An imaging system comprising:
   a multi-spectrum light source configured to form and direct a beam of light at multiple wavelengths at a specimen;
   a lens that combines reflected light from the specimen into a single beam of light along a single axis;
   a first optical filter disposed adjacent to the lens along the single axis and configured to filter e single beam of light at a first wavelength;
   a second optical filter disposed adjacent to the first optical filter along the single axis and configured to filter the single beam of light at a second wavelength;
   a first array sensor configured to detect the filtered single beam of light at the first wavelength from the first optical filter;
   a second array sensor configured to detect the filtered single beam of light at the second wavelength from the second optical filter;
   a computing device coupled to the first and second array sensor configured to:
   access first sensor data from the first array sensor;
   access second sensor data from the second array sensor;
   form a first image based on the first sensor data; the first image corresponding to the first wavelength;
   form a second image based on the second sensor data; the second image corresponding to the second wavelength; and
   form a composite image from the first image and the second image, the composite image registering a same pixel location in the composite image for both the first image and the second image.

2. The imaging system of claim 1, wherein the specimen comprises a tooth, wherein the first wavelength comprises human-visible light wavelength, wherein the second wavelength is at 900 nm or 1450 nm.

3. The imaging system of claim 2, wherein the computing device is further configured to:
   identify dental caries in the second image; and
   indicate the dental caries in the composite image.

4. The imaging system of claim 1, wherein the computing device is further configured to:
   generate a first plurality of images based on the first wavelength;
   generate a second plurality of images based on the second wavelength; and
   generate a three-dimensional model of the specimen based on the first and second plurality of images.

5. The imaging system of claim 1, wherein the first array sensor comprises a first two-dimensional optical sensor, wherein the second array sensor comprises a second two-dimensional optical sensor.

6. The imaging system of claim 1, wherein the first optical filter comprises a first semi-transparent mirror that filters every wavelengths except for the first wavelength, wherein the second optical filter comprises a second semi-transparent mirror that filters wavelengths based on the first wavelength.

7. A method comprising:
   directing a beam of light at multiple wavelengths, from a multi-spectrum light source, towards a specimen;
   combing reflected light from the specimen into a single beam of light with a lens disposed along a single axis of the single beam of light;
   filtering the single beam of light at a first wavelength with a first optical filter that is disposed adjacent to the lens along the single axis;
   filtering the single beam of light at a second wavelength with a second optical filter that is disposed adjacent to the first optical filter along the single axis;
   detecting, with a first array sensor, the filtered single beam of light at the first wavelength from the first optical filter;
   detecting, with a second array sensor, the filtered single beam of light at the second wavelength from the second optical filter;
   accessing first sensor data from the first array sensor;
   accessing second sensor data from the second array sensor;
   forming a first image based on the first sensor data;
   forming a second image based on the second sensor data; and
   forming a composite image from the first image and the second image, the composite image registering a same pixel location in the composite image for both the first image and the second image.

8. The method of claim 7, wherein the specimen comprises a tooth, wherein the first wavelength comprises human-visible light wavelength, wherein the second wavelength is at 900 nm or 1450 nm.

9. The method of claim 8, further comprising:
   identifying dental caries in the second image; and
   indicating the dental caries in the composite image.

10. The method of claim 7, further comprising:
    generating a first plurality of images based on the first wavelength;
    generating a second plurality of images based on the second wavelength; and
    generating a three-dimensional model of the specimen based on the first and second plurality of images.

11. The method of claim 7, wherein the first array sensor comprises a first two-dimensional optical sensor, wherein the second array sensor comprises a second two-dimensional optical sensor.

12. The method of claim 7, wherein the first optical filter comprises a first semi-transparent mirror that filters every wavelengths except for the first wavelength, wherein the second optical filter comprises a second semi-transparent mirror that filters wavelengths based on the first wavelength.

* * * * *

UNITED STATES PATENT AND TRADEMARK OFFICE
CERTIFICATE OF CORRECTION

| | |
|---|---|
| PATENT NO. | : 11,455,721 B2 |
| APPLICATION NO. | : 16/779021 |
| DATED | : September 27, 2022 |
| INVENTOR(S) | : Jang et al. |

It is certified that error appears in the above-identified patent and that said Letters Patent is hereby corrected as shown below:

On the Title Page

Item (71), in "Applicants", in Column 1, Line 3, delete "San Francisco," and insert --San Mateo,-- therefor In the Claims In Column 15, Line 9, in Claim 1, delete "e" and insert --the-- therefor In Column 15, Line 24, in Claim 1, delete "data;" and insert --data,-- therefor In Column 15, Line 26, in Claim 1, delete "data;" and insert --data,-- therefor Signed and Sealed this
Eighth Day of November, 2022

Katherine Kelly Vidal
*Director of the United States Patent and Trademark Office*